(12) United States Patent
Beilinson et al.

(10) Patent No.: US 10,947,556 B2
(45) Date of Patent: Mar. 16, 2021

(54) SEQUENCES TO FACILITATE INCORPORATION OF DNA INTO THE GENOME OF AN ORGANISM

(71) Applicant: AgBiome, inc., Research Triangle Park, NC (US)

(72) Inventors: Vadim Beilinson, Cary, NC (US); James R. Henriksen, Cary, NC (US)

(73) Assignee: AgBiome, Inc., Durham, NC (US)

( * ) Notice: Subject to any disclaimer, the term of this patent is extended or adjusted under 35 U.S.C. 154(b) by 73 days.

(21) Appl. No.: 15/535,750

(22) PCT Filed: Dec. 18, 2015

(86) PCT No.: PCT/US2015/066702
§ 371 (c)(1),
(2) Date: Jun. 14, 2017

(87) PCT Pub. No.: WO2016/100832
PCT Pub. Date: Jun. 23, 2016

(65) Prior Publication Data
US 2017/0369898 A1 Dec. 28, 2017

Related U.S. Application Data

(60) Provisional application No. 62/189,505, filed on Jul. 7, 2015, provisional application No. 62/094,697, filed on Dec. 19, 2014, provisional application No. 62/094,782, filed on Dec. 19, 2014.

(51) Int. Cl.
*C12N 15/82* (2006.01)
*C12N 9/10* (2006.01)
*A01N 57/20* (2006.01)

(52) U.S. Cl.
CPC ......... *C12N 15/8277* (2013.01); *A01N 57/20* (2013.01); *C12N 9/1029* (2013.01); *C12N 15/8209* (2013.01); *C12Y 203/01183* (2013.01)

(58) Field of Classification Search
None
See application file for complete search history.

(56) References Cited

U.S. PATENT DOCUMENTS

| | | | | |
|---|---|---|---|---|
| 7,598,430 B2 * | 10/2009 | Weeks | ................ | C12N 15/8205 435/469 |
| 8,344,208 B2 * | 1/2013 | Kearney | ............ | C12N 15/8203 435/320.1 |
| 10,066,235 B2 | 9/2018 | Gilbertson | | |
| 2005/0034188 A1 * | 2/2005 | Weeks | ...................... | C12N 9/88 800/278 |
| 2007/0271627 A1 * | 11/2007 | Ye | ...................... | C12N 15/8205 800/278 |
| 2013/0078706 A1 * | 3/2013 | Mullins | .............. | C12N 15/8202 435/252.3 |

FOREIGN PATENT DOCUMENTS

| | | |
|---|---|---|
| WO | 03/003816 | 1/2003 |
| WO | 2005/004585 | 1/2005 |
| WO | 2007/137075 | 11/2007 |

OTHER PUBLICATIONS

Haaren et al. (Plant Molecular Biology 13: 523-531, 1989). (Year: 1989).*
Conner et al. (Euphytica 154.3 (2007):341-353). (Year: 2007).*
Komori et al. (Plant physiology 145.4 (2007): 1155-1160. (Year: 2007).*
EBI Accession No. ADX69901, T-DNA border Seq ID No. 42, Apr. 21, 2005, 1 page.
International Search Report and Written Opinion of PCT/US2015/66702 dated Mar. 15, 2016, 13 pages.
Rudder et al., "Genome sequence of Ensifer adhaerens OV14 provides insights into its ability as a novel vector for the genetic transformation of plant genomes", BMC Genomics, vol. 15, Apr. 15, 2014, 17 pages.

* cited by examiner

*Primary Examiner* — Charles Logsdon
(74) *Attorney, Agent, or Firm* — Womble Bond Dickinson (US) LLP

(57) ABSTRACT

Methods and compositions are provided which allow for genetic modification of host cells including, plants and plant cells. The various methods and composition employ a recombinant DNA construct comprising SEQ ID NO: 1 and/or 2 or active variants and fragments thereof. Such polynucleotides find use in facilitating integration of polynucleotides of interest into the DNA of a host cell, including a plant or plant cell. Vectors, host cells, bacterium and plants comprising the recombinant DNA construct or fragments thereof are provided. Further provided are methods of introducing into a host cell or a plant cell a polynucleotide of interest. The method comprises contacting the host cell with a bacterium competent for the transformation of the host cell, wherein the bacterium comprises a transformation vector comprising a recombinant DNA construct.

23 Claims, 3 Drawing Sheets
Specification includes a Sequence Listing.

SEQUENCES TO FACILITATE INCORPORATION OF DNA INTO THE GENOME OF AN ORGANISM

CROSS REFERENCE TO RELATED APPLICATION

This Application claims the benefit of priority to U.S. Provisional Application No. 62/094,697, filed on Dec. 19, 2014, U.S. Provisional App. No. 62/094,782, filed Dec. 19, 2014, and U.S. Provisional Application No. 62/189,505, filed on Jul. 7, 2015, each of which are incorporated by reference in their entirety.

FIELD OF THE INVENTION

Methods and compositions are provided for the genetic modification of host cell, including plant cells.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named AgB009-PCT_SEQLIST.txt, created on Dec. 14, 2015, and having a size of 7.13 KB and is filed concurrently with the specification. The sequence listing contained in this ASCII formatted document is part of the specification and is herein incorporated by reference in its entirety.

BACKGROUND OF THE INVENTION

*Agrobacterium tumefaciens* is a widespread naturally occurring soil bacterium that causes crown gall, and has the ability to introduce new genetic material into the plant cell. The genetic material that is introduced is called T-DNA (transferred DNA) which is located on a Ti plasmid. A Ti plasmid is one type of conjugative mobile plasmid. Conjugative mobile plasmids are class of circular pieces of DNA that can facilitate their transfer between organisms and can be found in many different bacteria. This natural ability of the Ti plasmid to alter the plant's genetic makeup was the foundation of plant transformation using *Agrobacterium*.

Methods are needed in the art to provide other systems that allow for bacterial mediated transformation of plants or other host cells of interest.

BRIEF SUMMARY OF THE INVENTION

Methods and compositions are provided which allow for genetic modification of host cells, including plants and plant cells. The various methods and composition employ a recombinant DNA construct comprising SEQ ID NO: 1 and/or 2 or active variants and fragments thereof. Such polynucleotides find use in facilitating integration of polynucleotides of interest into the genomic DNA of a host cell, including a plant or plant cell. Vectors, host cells, bacterium and plants and plant cells comprising the recombinant DNA construct or variants and fragments thereof are provided. Further provided are methods of introducing a polynucleotide of interest into a host cell, including a plant cell. The method comprises contacting the host cell with a bacterium competent for the transformation of the host cell, wherein the bacterium comprises a transformation vector comprising a recombinant DNA construct. Other methods comprise contacting the plant cell with a bacterium competent for the transformation of the plant cell, where the bacterium comprises a plant transformation vector comprising a recombinant DNA construct provided herein.

DETAILED DESCRIPTION OF THE INVENTION

Figure 1:
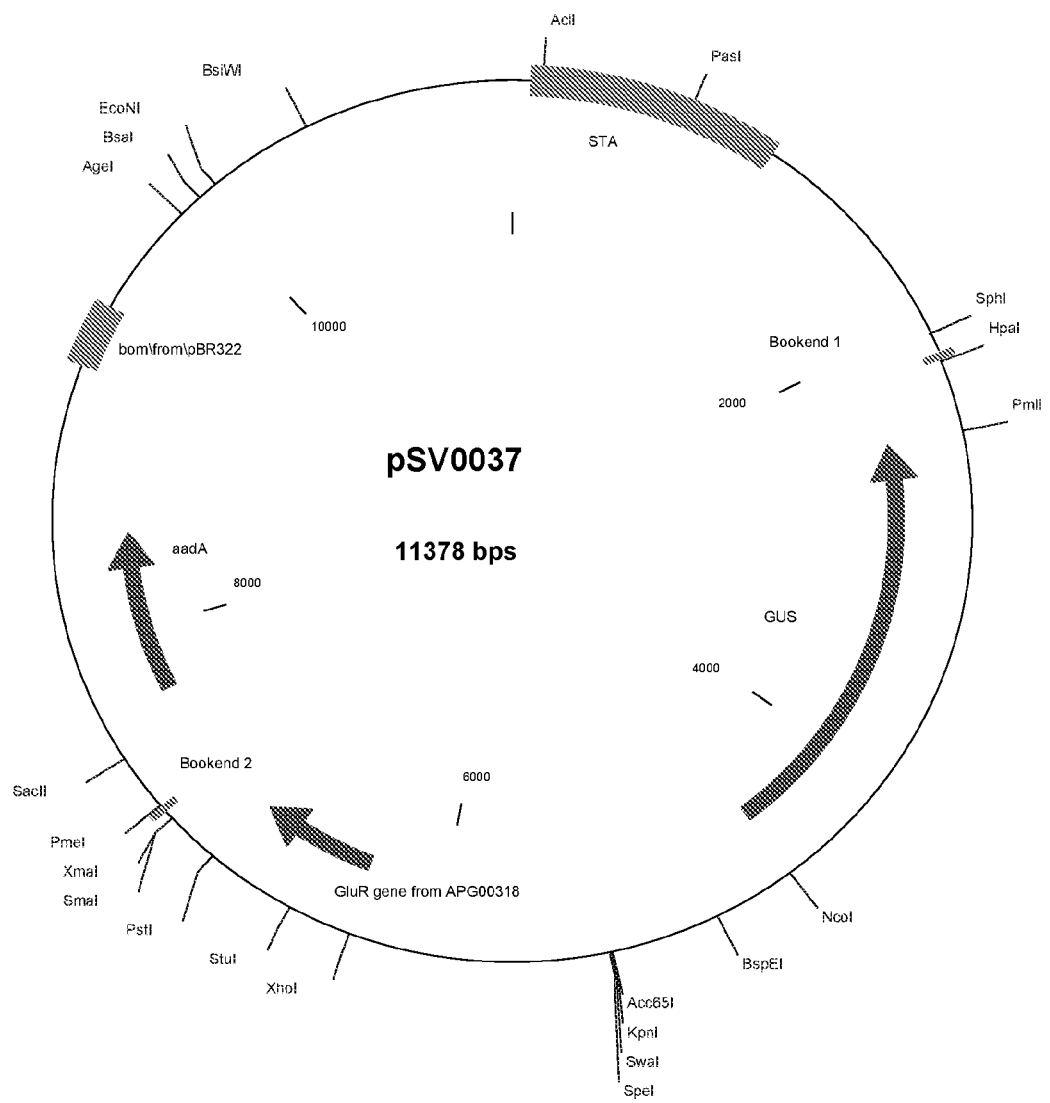
FIG. 1 provides a map of the transformation vector pSV0037.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I Compositions

A. DNA Integration Facilitating Sequences

Various polynucleotides that facilitate integration of a polynucleotide of interest in the DNA (i.e., genomic DNA) of a host cell, including a plant or a plant cell are provided. Such sequences are set forth in SEQ ID NO: 1 and 2, and are referred to herein as "bookend 1" and "bookend 2", respectively. As used herein, "DNA integration facilitation" refers to the ability of a sequence to promote the integration of an operably linked sequence into genomic DNA. Various methods to assay for this activity are discussed in further detail elsewhere herein.

Fragments and variants of a DNA integration facilitating sequence can be employed in the methods and compositions disclosed herein. By "fragment" is intended a portion of the polynucleotide. Fragments of SEQ ID NO: 1 or 2 may range from 24, 23, 22, 21, 20, 19, 18, 17, 16, 15, 14, 13, 12, 11, 10, 9, 8, 7, 6, or 5 nucleotides or less. In specific embodiments, active fragments of SEQ ID NO:1 or 2 are provided and thereby continue to facilitate DNA integration. In other instances, the fragments need not retain biologically activity. Such fragments may arise after DNA integration, and thereby leaving a "footprint" of SEQ ID NO:1 or 2 within the plant genomic DNA or within the genome of the host organism. Thus, such fragments can be detected in a plant genome or the other organism's genome following the use of the integration facilitation sequences.

"Variants" is intended to mean substantially similar sequences. For polynucleotides, a variant comprises a polynucleotide having a deletion (i.e., truncations) at the 5' and/or 3' end and/or a deletion and/or addition of one or more nucleotides at one or more internal sites within SEQ ID NO: 1 or 2 and/or a substitution of one or more nucleotides at one or more sites in SEQ ID NO: 1 or 2. Naturally occurring variants or synthetically derived polynucleotides, such as those generated, for example, by using site-directed mutagenesis or gene synthesis but which still retain the ability to facilitate DNA integration. In other instances, the variants need not retain biologically activity. Such variants may arise after DNA integration, and thereby leaving a footprint of the SEQ ID NO:1 or 2 within the plant genomic DNA or the host cell's DNA. Thus, such variants can be detected in a plant genome or in the host cell genome following the use of the integration facilitation sequences.

In other embodiments, biologically active variants will have a percent identity across their full length of at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the polynucleotide of any one of SEQ ID NO: 1 or 2 as determined by sequence alignment programs and parameters described elsewhere herein.

Methods for generating variants and fragments are generally known in the art. For example, methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein.

As used herein, an "isolated" or "purified" polynucleotide or biologically active portion thereof, is substantially or essentially free from components that normally accompany or interact with the polynucleotide as found in its naturally occurring environment. Thus, an isolated or purified polynucleotide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene is recombinant.

B. Recombinant Polynucleotide Constructs

The use of the term "polynucleotide" is not intended to limit the methods and compositions to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides employed herein also encompass all forms of sequences including, but not limited to, single-stranded forms, double-stranded forms, hairpins, stem-and-loop structures, and the like.

The various polynucleotides that facilitate integration of a polynucleotide of interest into the DNA (i.e., genomic DNA) or active variants or fragments thereof can be provided in recombinant DNA constructs. Such construct comprise SEQ ID NO: 1 and/or 2 or an active variant or fragment thereof operably linked to a polynucleotide of interest. "Operably linked" is intended to mean a functional linkage between two or more elements. Operably linked elements may be contiguous or non-contiguous. For example, in the context of a polynucleotide that facilitates DNA integration "operably linked" to the polynucleotide of interest refers to a linkage between the elements that is such as to allow for SEQ ID NO: 1, 2 or an active fragment or variant thereof to promote the integration of the polynucleotide sequence of interest into the DNA.

When the sequences that facilitate DNA integration flank the polynucleotide of interest, the bookends can be any distance from one another that allow for the integration of the polynucleotide of interest. In non-limiting embodiments, the flanking bookends are separated by at least about 25, 50, 75, 100, 200, 300, 400, 500, 600, 700, 900 nucleotide or at least 1 Kb, 2 kb, 3 kb, 4 kb, 5 kb, 6 kb, 7 kb, 10 kb, 15 kb, 20 kb, 40 kb, 60 kb or more.

Various recombinant DNA constructs can be generated employing the polynucleotide that facilitates integration of a polynucleotide of interest into the genome of a host cell. Such construct can comprise a recombinant DNA construct comprising a polynucleotide of interest operably linked to at least one of SEQ ID NO: 1 or SEQ ID NO:2, or an active variant or fragment thereof. In such instances, the DNA sequence that facilitates integration into the genomic DNA can be operably linked to the 5' end or to the 3' end of the polynucleotide of interest. In specific embodiments, the DNA construct comprises a polynucleotide of interest operably linked at its 3' end to SEQ ID NO: 2 or SEQ ID NO: 1 or an active variant or fragment thereof. Alternatively, the DNA construct comprises a polynucleotide of interest operably linked at its 5' end to SEQ ID NO: 2 or SEQ ID NO: 1 or an active variant or fragment thereof.

In other instances, the recombinant DNA constructs comprises a polynucleotide operably linked to the DNA integration sequences wherein the sequences that facilitate integration into the DNA flank the polynucleotide of interest. In such instances, SEQ ID NO: 1, 2, or an active variant or fragment thereof can be operably linked at the 5' end of the polynucleotide of interest and SEQ ID NO: 1, 2, or an active variant thereof can be operably linked to the 3' end of the polynucleotide of interest. In one specific embodiment, SEQ ID NO: 1 or an active variant or fragment thereof is operably linked to the 5' end of the polynucleotide of interest and SEQ ID NO: 2 or an active variant or fragment thereof is operably linked to the 3' end of the polynucleotide of interest.

Thus, non-limiting examples of recombinant DNA constructs of the invention may include a construct comprising SEQ ID NO: 1 or an active variant or fragment thereof operably linked 5' or 3' to a polynucleotide of interest. In other embodiments, the recombinant DNA construct comprises SEQ ID NO: 1 or an active variant or fragment thereof operably linked 5' and 3' to a polynucleotide of interest. In other embodiments, the recombinant DNA construct comprises SEQ ID NO: 2 or an active variant or fragment thereof operably linked 5' or 3' to a polynucleotide of interest. In other embodiments, the recombinant DNA construct comprises SEQ ID NO: 2 or an active variant or fragment thereof operably linked 5' and 3' to a polynucleotide of interest. In other embodiments, the recombinant DNA construct comprises SEQ ID NO: 1 and SEQ ID NO: 2 or active variants or fragments thereof operably linked to and flanking a polynucleotide sequence of interest where SEQ ID NO:1 is 5' to the polynucleotide sequence of interest and SEQ ID NO:2 is 3' to the polynucleotide sequence of interest. In other embodiments, the recombinant DNA construct comprises SEQ ID NO: 1 and SEQ ID NO: 2 or active variants or fragments thereof operably linked to and flanking a polynucleotide sequence of interest where SEQ ID NO: 2 is 5' to the polynucleotide sequence of interest and SEQ ID NO: 1 is 3' to the polynucleotide sequence of interest.

In each of these embodiments, the recombinant DNA construct and/or the plant transformation vector may contain either a right T-DNA border, or a left T-DNA border, or both a right and left T-DNA border, or no T-DNA border. In one embodiment, the DNA construct comprising the sequences that facilitate integration of the polynucleotide of interest does not contain a T-DNA border sequence. As used herein, a T-DNA "Border sequence," e.g. right border (RB) or left border (LB), refers to a directly repeated nucleic acid sequence defining an end of the transferred DNA (T-DNA) region, typically about 24 bp in length. Border sequences are from a Ti plasmid of *Agrobacterium* sp., typically *Agrobacterium tumefaciens*.

In other embodiments, the DNA construct comprises a combination of at least one T-DNA boarder sequence and one or more of the sequences that facilitate integration of the polypeptide of interest (i.e., SEQ ID NO: 1 or 2 or an active variant thereof). For example, the DNA construct can comprise in a 5' to 3' orientation at least one of SEQ ID NO: 1 or 2 or an active variant thereof, a polynucleotide of interest, and a right T-DNA border. In other embodiments, the DNA construct can comprise in a 5' to 3' orientation a left T-DNA border, a polynucleotide of interest, and at least one of SEQ ID NO: 1 or 2 or an active variant thereof. As used herein, "heterologous" in reference to a sequence is a sequence that originates from a foreign species, or, if from the same species, is modified from its native form in composition and/or genomic locus by deliberate human intervention. For example, the polynucleotide(s) that facilitates introduction of the polynucleotide sequence of interest into the genome is heterologous to the polynucleotide of interest.

i. Polynucleotides of Interest

The polynucleotide of interest (which can comprise one or more expression cassettes) can be of any length that allows for integration into the genomic DNA. In specific, non-limiting embodiments, the polynucleotide of interest can be at least about 25, 50, 100, 200, 300, 400, 500, 700, 900 nucleotide or at least 1 Kb, 2 kb, 3 kb, 4 kb, 5 kb, 6 kb, 7 kb, 8 kb, 9 kb, 10 kb, 11 kb, 12 kb, 13 kb, 14 kb, 15 kb, 20 kb, 40 kb, 60 kb or more. In other embodiments, the polynucleotide of interest is at least about 6 kb to about 15 kb, or about 6 kb to about 12 kb, or about 1 kb to about 12 kb.

Various changes in phenotype of the plant or plant cells are of interest upon introduction of the polynucleotide of interest. Such alterations include, but are not limited to, modifying the fatty acid composition in a plant, altering the amino acid content of a plant, altering a plant's pathogen defense mechanism, altering the plant's herbicide tolerance and the like. These results can be achieved by providing expression of heterologous products or increased expression of endogenous products in plants. Alternatively, the results can be achieved by providing for a reduction of expression of one or more endogenous products in the plant. These changes result in a change in phenotype of the transformed plant. To this end, the polynucleotide of interest can encode a protein or it can express a polynucleotide that acts to increase or decreases expression of a sequence of interest in the plant, and can include for example, miRNA or siRNA.

Genes of interest are reflective of the commercial markets and interests of those involved in the development of the crop. Crops and markets of interest change, and as developing nations open up world markets, new crops and technologies will emerge also. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like. See, for example, U.S. Pat. Nos. 5,703,049, 5,885, 801, 5,885,802, and 5,990,389, herein incorporated by reference. Other agronomically important genes encode latex, Floury 2, growth factors, seed storage factors, and transcription factors. Insect resistance genes may encode resistance to pests such as rootworm, cutworm, European Corn Borer, western corn root worm, fall army worm, corn ear worm, black cut worm, cotton ball worms, green stink bugs, soybean aphids, and/or nematodes, such as, soybean cyst nematodes or root not nematodes and the like. Such genes include, for example, Bacillus thuringiensis toxic protein genes (U.S. Pat. Nos. 5,366,892; 5,747,450; 5,736,514; 5,723,756; 5,593,881; and Geiser et al. (1986) *Gene* 48:109); and the like. Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like. Herbicide resistance traits may include genes coding for resistance to herbicides. Sterility genes can also be encoded in an expression cassette and provide an alternative to physical detasseling. U.S. Pat. No. 5,583,210. Other genes include kinases and those encoding compounds toxic to either male or female gametophytic development.

In other embodiments, the polynucleotide of interest may facilitate the transfer of non-agronomic traits. For example, the polynucleotide of interest can encodes non-agronomic proteins including antibodies for vaccines, micronutrients (e.g. folic acid, vitamin A), bio-pharmaceutical or veterinarian drugs.

It is recognized that the methods and compositions can be employed to integrate polynucleotides of interest into organism other than plants. Thus, any sequence can be employed as a polynucleotide of interest.

ii. Expression Cassettes

One or more polynucleotides can be contained in an expression cassette for expression in the plant of interest. The cassette can include 5' and 3' regulatory sequences operably linked to a polynucleotide of interest. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. Additional gene(s) can be provided on multiple expression cassettes. Such an expression cassette is provided with a plurality of restriction sites and/or recombination sites for insertion of the polynucleotide of interest.

The expression cassette can include in the 5'-3' direction of transcription, a transcriptional initiation region (i.e., a promoter) and a polynucleotide of interest. The expression cassettes may additionally contain 5' leader sequences. Such leader sequences can act to enhance translation. The regulatory regions (i.e., promoters, transcriptional regulatory regions, and translational termination regions) and/or the polynucleotide of interest with the various expression cassettes may be native/analogous to the host cell or to each other. Alternatively, the regulatory regions and/or the polynucleotide of interest may be heterologous to the host cell or to each other.

As used herein, "heterologous" in reference to a sequence is a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are modified from their original form and/or genomic locus, or the promoter is not the native promoter for the operably linked polynucleotide.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas. Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference in their entirety. The above list of selectable marker genes is not meant to be limiting.

Additional selectable markers that can be employed include those disclosed in U.S. Provisional Application No. 62/094,697, filed on Dec. 19, 2014 and U.S. Provisional Application No. 62/189,505, filed on Jul. 7, 2015, both of which are incorporated by reference in their entirety.

iii. Transformation Vectors

The recombinant DNA construct comprising the integration facilitating sequences of SEQ ID NO:1 and/or 2 or an active variant or fragment thereof operably linked to the polynucleotide of interest can be contained in a plasmid or vector. General methods for preparing plasmids or vectors that contain desired genetic components that can be used to transform host cells, including plants, and methods of making those vectors are known. Vectors typically consist of a number of genetic components, including, but not limited to, regulatory elements such as promoters, leaders, introns, and terminator sequences. Regulatory elements are also referred to as cis- or trans-regulatory elements, depending on the proximity of the element to the sequences or gene(s) they control. The promoter region contains a sequence of bases that signals RNA polymerase to associate with the DNA and to initiate the transcription into mRNA using one of the DNA strands as a template to make a corresponding complementary strand of RNA.

The plasmid or vectors may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene.

A "transformation platform" should be understood to mean the genetic machinery required to transfer a gene into cell. Thus, this term encompasses both the transformation vector, the bacteria competent for the transformation of the host cell, and any other components required for stable integration of the polynucleotide of interest into the genome of the host cell. Such components are discussed in further detail elsewhere herein.

In one embodiment, the transformation platform is a unitary transformation vector. In this specification, the term "unitary (transformation) vector" generally means a single transformation vector comprising a Ti plasmid and a transgene and ideally the required number of virulence genes. In another embodiment, the transformation vector is a binary vector system. The term "binary vector system" is taken to mean a Ti plasmid containing the transgene and a neighboring virulence plasmid containing the necessary vir genes to accommodate successful transformation.

In other embodiments, the unitary (transformation) vector comprises a Ti plasmid (that lacks the native T-DNA borders) and comprises a transgene and ideally the required number of virulence genes. In another embodiment, the binary vector system comprises a Ti plasmid (that lacks the native T-DNA borders) and comprises the transgene and a neighboring virulence plasmid containing the necessary vir genes to accommodate successful transformation.

II. Host Cells, Plants, Plant Parts, Seeds

By "host cell" is meant a cell which comprises the recombinant DNA construct provided herein. Host cells may be prokaryotic cells or eukaryotic cells.

Various bacterium can be used as a delivery system for the recombinant DNA construct comprising a polynucleotide of interest operably linked to SEQ ID NO: 1 and/or SEQ ID NO:2, or an active variant or fragment thereof into the plant cell. In one embodiment, the host bacterial strain can be an *Agrobacterium*. *Agrobacterium* strains may include, but are not limited to, disarmed derivatives of *A. tumefaciens* strain C58, a nopaline strain that is used to mediate the transfer of DNA into a plant cell; octopine strains, such as LBA4404; or agropine strains, e.g., EHA101, EHA105, or *R. leguminosarum* USDA2370 with a Ti or Ri plasmid. Other bacterial strains which can be used for plant transformation include *A. rhizogenes, Sinorhizobium* sp., *Mesorhizobium* sp., *Bradyrhizobium* sp., and *Rhizobium* sp. strains. In still other embodiments, the bacterium is *Ensifer adhaerens*, including for example strain OV14 having NCIMB deposit number NCIMB 41777. See, for example, Dheeraj Singh Rathore, Fiona Doohan. (2012) "Developing Ensifer-Mediated Transformation (EMT) as a Robust Platform for Genetic Manipulation of Crop Species"; Rudder et al. (2014) *BMC Genomics* 15: 268; Wendt et al. (2012) *Transgenic Research* 21: 567-78; and, US20130078706, each of which is herein incorporated by reference in their entirety. In still other non-limiting embodiments, the host bacterial strain is from *Sinorhizobium*, and in more specific embodiments, the host bacterial strain is from *Sinorhizobium fredii*, including for example, *Sinorhizobium fredii* SF4404 and *Sinorhizobium fredii* SF542C. See, for example, WO2007137075 which is herein incorporated by reference in its entirely.

Non-limiting examples of recombinant DNA constructs of the invention may include a construct comprising SEQ ID NO: 1 or an active variant or fragment thereof operably linked 5' or 3' to a polynucleotide of interest. In other embodiments, the recombinant DNA construct comprises SEQ ID NO: 1 or an active variant or fragment thereof operably linked 5' and 3' to a polynucleotide of interest. In other embodiments, the recombinant DNA construct comprises SEQ ID NO: 2 or an active variant or fragment thereof operably linked 5' or 3' to a polynucleotide of interest. In other embodiments, the recombinant DNA construct comprises SEQ ID NO: 2 or an active variant or fragment thereof operably linked 5' and 3' to a polynucleotide of interest. In other embodiments, the recombinant DNA construct comprises SEQ ID NO: 1 and SEQ ID NO: 2 or active variants or fragments thereof operably linked to and flanking a polynucleotide sequence of interest where SEQ ID NO:1 is 5' to the polynucleotide sequence of interest and SEQ ID NO:2 is 3' to the polynucleotide sequence of interest. In other embodiments, the recombinant DNA construct comprises SEQ ID NO: 1 and SEQ ID NO: 2 or active variants or fragments thereof operably linked to and flanking a polynucleotide sequence of interest where SEQ ID NO: 2 is 5' to the polynucleotide sequence of interest and SEQ ID NO: 1 is 3' to the polynucleotide sequence of interest. In each of these embodiments, the recombinant DNA construct and/or the plant transformation vector may contain either a right T-DNA border, or a left T-DNA border, or both a right and left T-DNA border, or no T-DNA border.

In other embodiments, the host cell is a plant cell. It is understood, that upon integration of the recombinant DNA construct into the genomic DNA of the plant cell a footprint (or fragment) of SEQ ID NO:1 and/or 2 may be integrated into the genome of the host plant cell. Thus, various plants, plant cells, and seeds having such a footprint are provided herein.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides of interest and a least a footprint of SEQ ID NO: 1 and/or 2 or a variant or fragment thereof.

As used herein, a "footprint" of SEQ ID NO: 1 and/or 2 comprises or consist of at least 8, 9, 10, 11, 12, 13, 14, 15, 16, 17, 18, 19, 20, 21, 22, 23, 24, or 25 contiguous nucleotides of SEQ ID NO: 1 and/or 2 or a variant thereof, wherein said footprint is contiguous with the expression vector comprising the polynucleotide of interest. In specific embodiments, the footprint comprises at least a 5' fragment of the right bookend and/or at least a 3' fragment of the left bookend, wherein said footprint is contiguous with the expression vector comprising the polynucleotide of interest.

Any plant species can be used in the methods and compositions disclose herein, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are of interest.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same germplasm, variety or line as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

In other embodiments, the host cell can comprise a prokaryotic cell, a eukaryotic cell, a fungus, or bacteria.

III. Method of Introducing

Various methods can be used to introduce the recombinant DNA construct into a host cell, plant or plant part. "Introducing" is intended to mean presenting to the host cell, plant, plant cell or plant part the polynucleotide or polypeptide in such a manner that the sequence gains access to the interior of a cell.

"Stable transformation" is intended to mean that the nucleotide construct introduced into a host cell or plant integrates into the genome of the host cell or plant and is capable of being inherited by the progeny thereof "Transient transformation" is intended to mean that a polynucleotide is introduced into the host cell or plant and does not integrate into the genome of the host cell or plant or a polypeptide is introduced into a host cell or plant.

Various methods are provided to transform a plant cell. The methods comprise introducing into the plant cell the polynucleotide of interest by bacterially mediated transformation, wherein the bacteria is competent for the transformation of the plant cell and the bacteria comprises a plant transformation vector comprising a recombinant DNA construct comprising a polynucleotide of interest operably linked to one or more of the sequence that facilitate DNA integration disclosed herein.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J*. 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet*. 22:421-477; Sanford et al. (1987) *Particulate Science and Technology* 5:27-37 (onion); Christou et al. (1988) *Plant Physiol*. 87:671-674 (soybean); McCabe et al. (1988) *Bio/Technology* 6:923-926 (soybean); Finer and McMullen (1991) *In Vitro Cell Dev. Biol*. 27P:175-182 (soybean); Singh et al. (1998) *Theor. Appl. Genet*. 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol*. 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet*. 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference in their entirety.

In other instances, the method of transformation employed for soybean is set forth in U.S. Pat. No. 7,473,822 and/or Paz et. al. (2010) "*Agrobacterium-mediated transformation of soybean and recovery of transgenic soybean plants*" Plant Transformation Facility at University of Iowa, 1-6, both of which are herein incorporated by reference in their entirety.

In other embodiments, the a recombinant DNA construct comprising a polynucleotide of interest operably linked to one or more of the sequence that facilitate DNA integration disclosed herein may be introduced into plants by contacting plants with a virus or viral nucleic acids. Generally, such methods involve incorporating a nucleotide construct of the invention within a DNA or RNA molecule. It is recognized that the sequence may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference in their entirety.

After the construction of the plant transformation vector or construct, the nucleic acid molecule, prepared as a DNA composition in vitro, is generally introduced into a suitable host such as Escherichia coli and mated into another suitable host or electroporated directly into a suitable host (i.e., a bacteria competent for plant transformation) such as, but not limited to, *Sinorhizobium, Sinorhizobium fredii, Agrobacterium, A. rhizogenes, Sinorhizobium* sp., *Mesorhizobium* sp., *Bradyrhizobium* sp., *Rhizobium* sp. or *Ensifer*. These techniques are known to those of skill in the art and have been described for a number of plant systems including soybean, cotton, and wheat (see, for example, U.S. Pat. Nos. 5,569,834 and 5,159,135 and WO 97/48814).

In one embodiment, the vector is then introduced into a plant cell by bacterially mediated transformation. The given bacteria employed in such methods is competent for the transformation of the plant cell. Plant tissue to be transformed is typically inoculated and co-cultured with a bacteria competent for plant transformation which contains a recombinant construct comprising at least one heterologous DNA integration facilitating (SEQ ID NO: 1 and/or 2 or an active variant or fragment thereof) operably linked to a polynucleotide sequence of interest to be transferred. Transformed cell are selected under appropriate conditions.

In other embodiments, the vector can be introduced into a host cell of interest by bacterially mediated transformation. The given bacteria employed in such methods is competent for the transformation of the host cell.

The recombinant DNA constructs comprising at least one heterologous DNA integration facilitating (SEQ ID NO: 1 and/or 2 or an active variant or fragment thereof) operably linked to a polynucleotide sequence of interest or plasmids and vector comprising the same can be used with any transformable cell or tissue. Transformable plant tissue generally refers to tissue that can have exogenous DNA inserted in its genome and under appropriate culture conditions can form into a differentiated plant. Such tissue can include, but is not limited to, cell suspensions, callus tissue, hypocotyl tissue, cotyledons, embryos, meristematic tissue, roots, and leaves. For example, transformable tissues can include calli or embryoids from anthers, microspores, inflorescences, and leaf tissues.

Methods for transforming plants by use of a bacterial mediated transformation and obtaining transgenic plants have been published for a number of crops including in dicots and monocots. Such plants include, for example, cotton, soybean, *Brassica*, peanut, asparagus, barley, maize, oat, rice, sugarcane, tall fescue, and wheat. See for example, methods for use in the context of cotton transformation are disclosed in U.S. Pat. Nos. 5,846,797, 5,159,135, 5,004,863, and 6,624,344; methods for use for transforming *Brassica* plants are disclosed, for example, in U.S. Pat. No. 5,750,871; methods for the use of techniques for transforming soybean are disclosed in for example in Zhang et al., (1999) and U.S. Pat. No. 6,384,301; and methods for transforming corn are disclosed in for example in U.S. Pat. Nos. 5,981,840, 7,060,876, 5,591,616, WO95/06722, and U.S. Patent Pub. 2004/244075. Each of these references is herein incorporated by reference in their entirety.

In one embodiment, after incubation on medium containing antibiotics to inhibit bacterial growth without selective agents, the explants are cultured on selective growth medium including, but not limited to, a callus-inducing medium containing a plant cell selective agent. Typical selective agents have been described and include, but are not limited to, antibiotics such as G418, paromomycin, kanamycin, or other chemicals such as glyphosate, dicamba, and glufosinate. The plant tissue cultures surviving the selection medium are subsequently transferred to a regeneration medium suitable for the production of transformed plantlets. Regeneration can be carried out over several steps. Those of skill in the art are aware of the numerous types of media and transfer requirements that can be implemented and optimized for each plant system for plant transformation and regeneration.

The transformants produced are subsequently analyzed to determine the presence or absence of a particular nucleic acid of interest contained on the transformation vector. The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

IV. Sequence Comparisons

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Additional mathematical algorithms are known in the art and can be utilized for the comparison of two sequences. See, for example, the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLAST programs of Altschul et al. (1990) J. Mol. Biol. 215:403. BLAST nucleotide searches can be performed with the BLASTN program. BLAST protein searches can be performed with the BLASTP program. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

As used herein, the term "identity" or "percent identity" when used with respect to a particular pair of aligned amino acid or nucleotide sequences, refers to the percent amino acid sequence identity or the percent nucleotide sequence identity that is obtained by counting the number of identical matches in the alignment and dividing such number of identical matches by the length of the aligned sequences. As used herein, the term "similarity" or "percent similarity" when used with respect to a particular pair of aligned amino acid sequences or nucleotides sequences, refers to the sum of the scores that are obtained from a scoring matrix for each amino acid pair in the alignment divided by the length of the aligned sequences.

Unless otherwise stated, identity and similarity will be calculated by the Needleman-Wunsch global alignment and scoring algorithms (Needleman and Wunsch, 1970, J. Mol. Biol. 48(3):443-453) as implemented by the "needle" program, distributed as part of the EMBOSS software package (Rice, P. Longden, I. and Bleasby, A., EMBOSS: The European Molecular Biology Open Software Suite, 2000, Trends in Genetics 16, (6) pp 276-277, versions 6.3.1 available from EMBnet at EMBOSS web sites, among other sources) using default gap penalties and scoring matrices (EBLOSUM62 for protein and EDNAFULL for DNA). Equivalent programs may also be used. By "equivalent program" is intended any sequence comparison program that, for any two sequences in question, generates an alignment having identical nucleotide residue matches and an identical percent sequence identity when compared to the corresponding alignment generated by needle from EMBOSS version 6.3.1.

Non-limiting embodiments include:

1. A recombinant DNA construct comprising a polynucleotide of interest operably linked to SEQ ID NO: 1 or SEQ ID NO:2, or an active variant thereof comprising a sequence having at least 92% sequence identity to SEQ ID NO: 1 or 2, wherein said active variant facilitates integration of the polynucleotide of interest into DNA.

2. The recombinant DNA construct of embodiment 1, wherein SEQ ID NO: 1 or the active variant thereof is 5' to the polynucleotide of interest.

3. The recombinant DNA construct of embodiment 1, wherein SEQ ID NO: 1 or the active variant thereof is 3' to the polynucleotide of interest.

4. The recombinant DNA construct of embodiment 1, wherein SEQ ID NO: 1 or the active variant thereof is 5' and 3' to the polynucleotide of interest.

5. The recombinant DNA construct of embodiment 1, wherein SEQ ID NO: 2 or the active variant thereof is 5' to the polynucleotide of interest.

6. The recombinant DNA construct of embodiment 1, wherein SEQ ID NO: 2 or the active variant thereof is 3' to the polynucleotide of interest.

7. The recombinant DNA construct of embodiment 1, wherein SEQ ID NO: 2 or the active variant thereof is 5' and 3' to the polynucleotide of interest.

8. The recombinant DNA construct of embodiment 1, wherein SEQ ID NO: 1 and SEQ ID NO: 2 or the active variant thereof flank the polynucleotide sequence of interest.

9. The recombinant DNA construct of embodiment 8, wherein SEQ ID NO: 2 or the active variant thereof is 3' to the polynucleotide of interest and SEQ ID NO:1 or the active variant thereof is 5' to the polynucleotide of interest.

10. The recombinant DNA construct of embodiment 8, wherein SEQ ID NO: 2 or the active variant thereof is 5' to the polynucleotide of interest and SEQ ID NO:1 or the active variant thereof is 3' to the polynucleotide of interest.

11. The recombinant DNA construct of any one of embodiments 1-10, wherein said DNA construct does not contain a T-DNA border sequence.

12. A plant transformation vector comprising the recombinant DNA construct of any one of embodiments 1-11.

13. A bacterium comprising the plant transformation vector of embodiment 12.

14. The bacterium of embodiment 13, wherein the bacterium is *Sinorhizobium*.

15. The bacterium of embodiment 13, wherein the bacterium is *Agrobacterium*.

16. The bacterium of embodiment 13, wherein the bacterium is *Rhizobium*.

17. The bacterium of embodiment 13, wherein the bacterium is *Ensifer*.

18. A method of introducing into a plant cell a polynucleotide of interest comprising contacting the plant cell with a bacterium competent for the transformation of the plant cell, where the bacterium comprises a plant transformation vector comprising a recombinant DNA construct comprising a polynucleotide of interest operably linked to SEQ ID NO: 1 and/or SEQ ID NO:2 or an active variant thereof comprising a sequence having at least 92% sequence identity to SEQ ID NO: 1 and/or 2, wherein said active variant facilitates integration of the polynucleotide of interest into DNA.

19. The method of embodiment 18, further comprising selectively screening for a plant cell having integrated the polynucleotide of interest into its genome.

20. The method of embodiment 18 or 19, further comprising isolating a plant cell having the polynucleotide of interest integrated in its genome.

21. The method of any one of embodiments 18-20, wherein SEQ ID NO: 2 or the active variant thereof is 3' to the polynucleotide of interest.

22. The method of any one of embodiments 18-20, wherein SEQ ID NO: 2 or the active variant thereof is 5' to the polynucleotide of interest.

23. The method of any one of embodiments 18-20, wherein SEQ ID NO: 2 or the active variant thereof is 5' and 3' to the polynucleotide of interest.

24. The method of any one of embodiments 18-20, wherein SEQ ID NO: 1 or the active variant thereof is 3' to the polynucleotide of interest.

25. The method of any one of embodiments 18-20, wherein SEQ ID NO: 1 or the active variant thereof is 5' to the polynucleotide of interest.

26. The method of any one of embodiments 18-20, wherein SEQ ID NO: 1 or the active variant thereof is 5' and 3' to the polynucleotide of interest.

27. The method of any one of embodiments 18-20, wherein SEQ ID NO: 1 and SEQ ID NO: 2 or the active variant thereof flank the polynucleotide sequence of interest.

28. The method of embodiment 27, wherein SEQ ID NO: 2 or the active variant thereof is 3' to the polynucleotide of interest and SEQ ID NO:1 or the active variant thereof is 5' to the polynucleotide of interest.

29. The method of embodiment 27, wherein SEQ ID NO: 1 or the active variant thereof is 3' to the polynucleotide of interest and SEQ ID NO:2 or the active variant thereof is 5' to the polynucleotide of interest.

30. The method of any one of embodiments 18-29, wherein said DNA construct does not contain a T-DNA border sequence.

31. The method of any one of embodiments 18-30, wherein the bacterium is *Agrobacterium*.

32. The method of any one of embodiments 18-30, wherein the bacterium is *Rhizobium*.

33. The method of any one of embodiments 18-30, wherein the bacterium is *Sinorhizobium*.

34. The method of any one of embodiments 18-30, wherein the bacterium is *Ensifer*.

35. The method of any one of embodiments 18-34, wherein said plant cell is from a monocot.

36. The method of embodiment 35, wherein said monocot is maize, wheat, rice, barley, sorghum, or rye.

37. The method of any one of embodiments 18-34, wherein said plant cell is a from a dicot.

38. The method of embodiment 37, wherein said dicot is soybean, *Brassica*, sunflower, cotton, or alfalfa.

EXPERIMENTAL

Example 1

Genomic DNA of bacterial strain that belongs to Sinorhizobium fredii species, was sequenced and two DNA fragments (bookend 1 and bookend 2) were found.

```
Bookend 1:
                                  (SEQ ID NO: 1)
5'-TGGCAGGATATATGCTGGTGTAAAC-3'
and Bookend 2:
                                  (SEQ ID NO: 2)
5'-TGGCAGGATATATGTTGGTGTAACC-3'.
```

These, almost homologous repetitive sequences (2 mismatches—see table 1), were flanking about 5400 nucleotides of a DNA fragment that amongst other genes, had homolog to the VirD2 gene. These sequences were used to facilitate DNA integration into plant cells from Agrobacteria that had a plasmid with a glufosinate resistance gene driven by the CaMV 35S promoter. SEQ ID NO: 3 provides the sequence of the DNA construct comprising the bookends and the polynucleotide sequence of interest. Vectors that were used had either: (1) both Bookends flanking the DNA insert or (2) having Bookend 1 at the 5' of the DNA insert and Bookend 2 at the 3' of the insert, or (3) just a Bookend 2 only at the 3' end of the DNA insert. Transgenic soybean plants were selected on glufosinate containing media and used for further analysis.

TABLE 1

Alignment of SEQ ID NO: 1 and 2.
Underlined nucleotides denote mismatches.

TGGCAGGATATATG<u>C</u>TGGTGTAA<u>A</u>C

TGGCAGGATATATG<u>T</u>TGGTGTAA<u>CC</u>

Example 2

Genes having high tolerance level to glufosinate were cloned into 3 separate plant transformation vectors that carry Bookend 1 and Bookend 2 sequences which facilitate the integration of genes of interest into plant genomic DNA. Genetic material between Bookends was composed of two gene cassettes, one cassette with glufosinate resistant selectable marker, and one carrying GUS for the easy of trangenesis detection by staining plant material. See FIG. 1.

Figure 2:
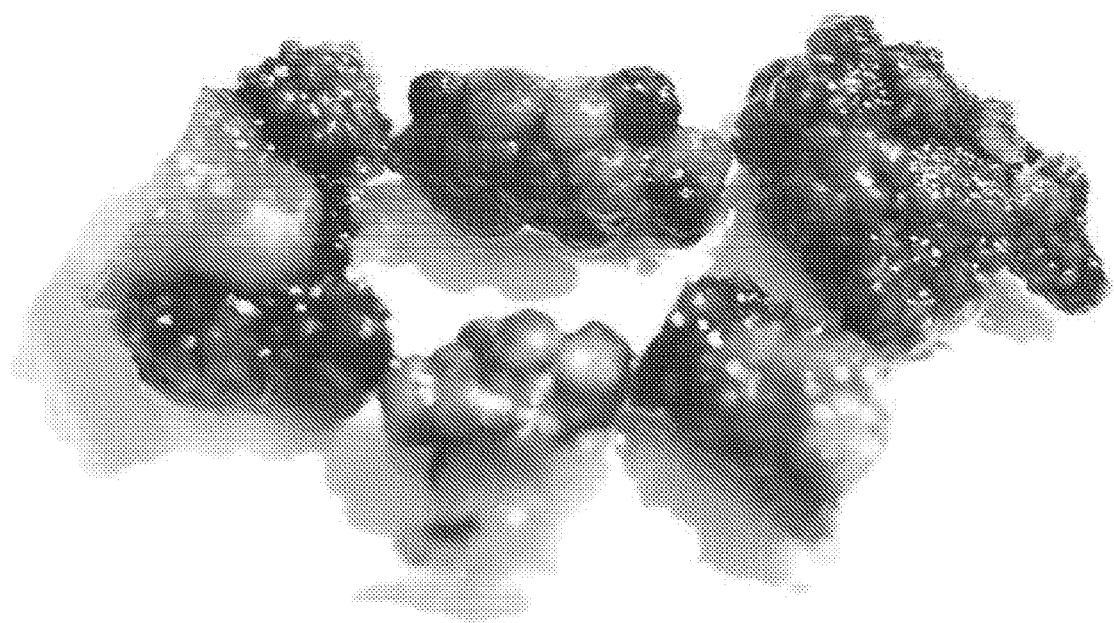
FIG. 2 provides a photo of transgenic soy callus employing the vector disclosed herein. Transgenic plants were selected by incubating callus on 25 uM glufosinate containing media. Glufosinate resistance was observed as soy callus was growing on the media, and transgenic nature of the callus was confirmed by staining the callus pieces with GUS stain.
Figure 3:
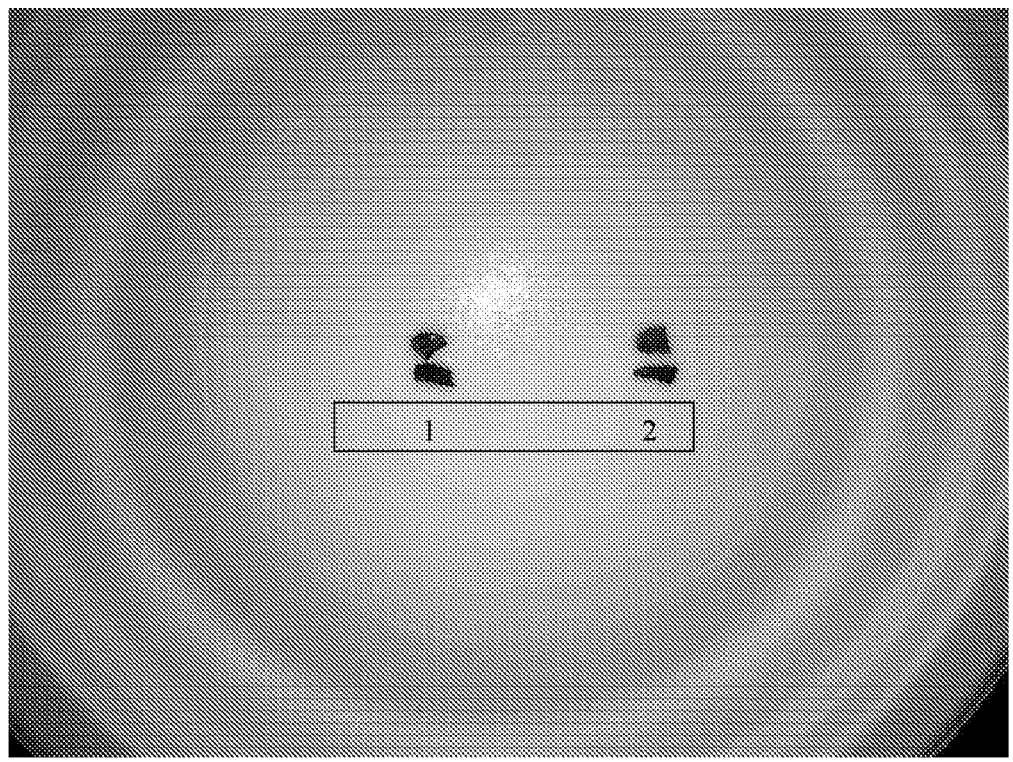
FIG. 3 provides GUS staining of leaf pieces excised from soybean plants transformed with pSV0037.

Transgenic plants were selected by incubating callus on 25 uM glufosinate containing media. Glufosinate resistance was observed as soy callus was growing on the media, and transgenic nature of the callus was confirmed by staining the callus pieces with GUS stain (see FIG. 2). GUS staining of leaf pieces excised from soybean plants transformed with pSV0037 are shown in FIG. 3.

Methods

Preparation of *Agrobacterium*: Four days prior to inoculation, several loops of *Agrobacterium* were streaked to a fresh plate of YEP* medium supplemented with the appropriate antibiotics (e.g., spectinomycin, chloramphenicol and kanamycin). Bacteria were grown for two days in the dark at 28 C. After two days, several loops of bacteria were transferred to 3 ml of YEP liquid medium with antibiotics in a 125 ml Erlenmeyer flask. Flasks were placed on a rotary shaker at 250 RPM at 28 C overnight. One day before inoculation, 2-3 ml of the overnight culture were transferred to 125 ml of YEP with antibiotics in a 500 ml Erlenmeyer flask. Flasks were placed on a rotary shaker at 250 RPM at 28 C overnight.

Prior to inoculation, the OD of the bacterial culture was checked at OD 620. An OD of 0.8-1.0 indicated that the culture is in log phase. The culture was centrifuged at 4000 RPM for 10 minutes in Oakridge tubes. The supernatant was discarded and the pellet is re-suspended in a volume of Soybean Infection Medium (SI) to achieve the desired OD. The cultures are held with periodic mixing until needed for inoculation.

Sterilization and Germination of Seeds: Two or three days prior to inoculation, soybean seeds were surface sterilized using chlorine gas. In a fume hood, a petri dish with seeds was place in a bell jar with the lid off 1.75 ml of 12 N HCl was slowly added to 100 ml of bleach in a 250 ml Erlenmeyer flask inside the bell jar. The lid was immediately placed on top of the bell jar. Seeds are allowed to sterilize for 14-16 hours (overnight). The top was removed from the bell jar and the lid of the petri dish is replaced. The petri dish with the surface sterilized was then opened in a laminar flow for around 30 minutes to disperse any remaining chlorine gas.

Seeds were imbibed with either sterile DI water or soybean infection medium (SI) for 1-2 days. Twenty to 30 seeds were covered with liquid in a 100×25 mm petri dish and incubated in the dark at 24 C. After imbibition, non-germinating seeds were discarded.

Preparation of Soybean Cotyledonary Explants: Cotyledonary explants were processed on a sterile paper plate with sterile filter paper dampened using SI medium. Cotyledonary explants were prepared employing techniques in the art. See, for example, U.S. Pat. No. 7,473,822, herein incorporated by reference.

Inoculation of Soybean Cotyledonary Explants: Typically, 16-20 cotyledons were inoculated per treatment. The SI medium used for holding the explants was discarded and replaced with 25 ml of *Agrobacterium* culture (OD 620=0.8-20). After all explants were submerged, the inoculation was carried out for 30 minutes with periodic swirling of the dish. After 30 minutes, the *Agrobacterium* culture was removed.

Co-cultivation of Soybean Cotyledonary Explants: Co-cultivation plates were prepared by overlaying one piece of sterile paper onto Soybean Co-cultivation Medium (SCC). Without blotting, the inoculated cotyledons were cultured adaxial side down on the filter paper. Around 20 explants can be cultured on each plate. The plates were sealed with Parafilm and cultured at 24 C and around 120 umoles m-2s-1 (in a Percival incubator) for 4-5 days.

Shoot Induction of Soybean Cotyledonary Explants:

After co-cultivation, the cotyledons were washed 3 times in 25 ml of Soybean Wash Medium with 200 mg/l of cefotaxime and timentin. The cotyledons were blotted on sterile filter paper and then transferred to Soybean Shoot Induction Medium (SSI). The nodal end of the explant was depressed slightly into the medium with distal end kept above the surface at about 45 deg. No more than 10 explants were cultured on each plate. The plates were wrapped with Micropore tape and cultured in the Percival at 24 C and around 120 umoles m-2s-1.

The explants were transferred to fresh SSI medium after 14 days. Emerging shoots from the shoot apex and cotyledonary node were discarded. Shoot induction was continued for another 14 days under the same conditions.

Shoot Elongation of Soybean Cotyledonary Explants: After 4 weeks of shoot induction, the cotyledon was separated from the nodal end and a parallel cut is made underneath the area of shoot induction (shoot pad). The area of the parallel cut was placed on Soybean Shoot Elongation Medium (SSE) and the explants cultured in the Percival at 24 C and around 120 umoles m-2s-1. This step was repeated every two weeks for up to 8 weeks as long as shoots continue to elongate.

Rooting of Transgenic Shoots: When shoots reach a length of 2-3 cm, they were transferred to Soybean Rooting Medium (SR) in a Plantcon vessel and incubated under the same conditions for 2 weeks or until roots reach a length of around 3-4 cm. After this, plants were transferred to soil.

Note, all media mentioned for soybean transformation are found in Paz et al. (2010) *Agrobacterium*-mediated transformation of soybean and recovery of transgenic soybean plants; Plant Transformation Facility of Iowa State University, which is herein incorporated by reference in its entirety.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant DNA construct comprising a polynucleotide of interest
   (a) operably linked to SEQ ID NO: 1 or an active variant thereof comprising a sequence having at least 93% sequence identity to SEQ ID NO: 1; and
   (b) operably linked to SEQ ID NO: 2 or an active variant thereof comprising a sequence having at least 93% sequence identity to SEQ ID NO: 2;
   wherein said active variant or variants facilitate integration of the polynucleotide of interest into DNA, and wherein SEQ ID NO: 1 or the active variant thereof and SEQ ID NO: 2 or the active variant thereof flank the polynucleotide of interest.

2. The recombinant DNA construct of claim 1, wherein SEQ ID NO: 2 or the active variant thereof is 3' to the polynucleotide of interest and SEQ ID NO:1 or the active variant thereof is 5' to the polynucleotide of interest.

3. The recombinant DNA construct of claim 1, wherein SEQ ID NO: 2 or the active variant thereof is 5' to the polynucleotide of interest and SEQ ID NO:1 or the active variant thereof is 3' to the polynucleotide of interest.

4. A plant transformation vector comprising the recombinant DNA construct of claim 1.

5. A bacterium comprising the plant transformation vector of claim 4.

6. The bacterium of claim 5, wherein the bacterium is a *Sinorhizobium* species bacterium.

7. The bacterium of claim 5, wherein the bacterium is an *Agrobacterium* species bacterium.

8. The bacterium of claim 5, wherein the bacterium is a *Rhizobium* species bacterium.

9. The bacterium of claim 5, wherein the bacterium is an Ensifer species bacterium.

10. A method of introducing into a plant cell a polynucleotide of interest comprising contacting the plant cell with a bacterium competent for the transformation of the plant cell, where the bacterium comprises a plant transformation vector comprising a recombinant DNA construct comprising a polynucleotide of interest
    (a) operably linked to SEQ ID NO: 1 or an active variant thereof comprising a sequence having at least 93% sequence identity to SEQ ID NO: 1; and
    (b) operably linked to SEQ ID NO: 2 or an active variant thereof comprising a sequence having at least 93% sequence identity to SEQ ID NO: 2;
    wherein said active variant or variants facilitate integration of the polynucleotide of interest into DNA, and wherein SEQ ID NO: 1 or the active variant thereof and SEQ ID NO: 2 or the active variant thereof flank the polynucleotide of interest.

11. The method of claim 10 further comprising selectively screening for a plant cell having integrated the polynucleotide of interest into its genome.

12. The method of claim 10, further comprising isolating a plant cell having the polynucleotide of interest integrated in its genome.

13. The method of claim 10, wherein SEQ ID NO: 2 or the active variant thereof is 3' to the polynucleotide of interest and SEQ ID NO:1 or the active variant thereof is 5' to the polynucleotide of interest.

14. The method of claim 10, wherein SEQ ID NO: 1 or the active variant thereof is 3' to the polynucleotide of interest and SEQ ID NO:2 or the active variant thereof is 5' to the polynucleotide of interest.

15. The method of claim 10, wherein said DNA construct does not contain a T-DNA border sequence.

16. The method of claim 10, wherein the bacterium is an *Agrobacterium* species bacterium.

17. The method of claim 10, wherein the bacterium is a *Rhizobium* species bacterium.

18. The method of claim 10, wherein the bacterium is a *Sinorhizobium* species bacterium.

19. The method of claim 10, wherein the bacterium is an Ensifer species bacterium.

20. The method of claim 10, wherein said plant cell is from a monocot.

21. The method of claim 20, wherein said monocot is maize, wheat, rice, barley, sorghum, or rye.

22. The method of claim 10, wherein said plant cell is from a dicot.

23. The method of claim 22, wherein said dicot is soybean, *Brassica*, sunflower, cotton, or alfalfa.

* * * * *

SEQUENCE LISTING

<160> NUMBER OF SEQ ID NOS: 3

<210> SEQ ID NO 1
<211> LENGTH: 25
<212> TYPE: DNA
<213> ORGANISM: Sinorhizobium fredii

<400> SEQUENCE: 1
tggcaggata tatgctggtg taaac                                25

<210> SEQ ID NO 2
<211> LENGTH: 25
<212> TYPE: DNA
<213> ORGANISM: Sinorhizobium fredii

<400> SEQUENCE: 2
tggcaggata tatgttggtg taacc                                25

<210> SEQ ID NO 3
<211> LENGTH: 5110
<212> TYPE: DNA
<213> ORGANISM: Artificial Sequence
<220> FEATURE:

<223> OTHER INFORMATION: DNA construct
<220> FEATURE:
<223> OTHER INFORMATION: bookend 2 (in reverse)
<220> FEATURE:
<223> OTHER INFORMATION: bookend 1 (in reverse)
<220> FEATURE:
<223> OTHER INFORMATION: NOS terminator (in reverse)
<220> FEATURE:
<223> OTHER INFORMATION: GUS gene with intron (in reverse)
<220> FEATURE:
<223> OTHER INFORMATION: CaMV 35S promoter (in reverse)
<220> FEATURE:
<223> OTHER INFORMATION: 2XCaMV 35S Promoter
<220> FEATURE:
<223> OTHER INFORMATION: glufosinate resitance gene
<220> FEATURE:
<223> OTHER INFORMATION: CaMV 35S terminator and polyA

<400> SEQUENCE: 3

```
ggttacacca acatatatcc tgccaaacac tgatagttaa ctaattcccg atctagtaac      60
atagatgaca ccgcgcgcga taatttatcc tagtttgcgc gctatatttt gttttctatc     120
gcgtattaaa tgtataattg cgggactcta atcataaaaa cccatctcat aaataacgtc     180
atgcattaca tgttaattat tacatgctta acgtaattca acagaaatta tatgataatc     240
atcgcaagac cggcaacagg attcaatctt aagaaacttt attgccaaat gtttgaacga     300
tcggggaaat tcgagctggt cacctgtaat tcacacgtgg tggtggtggt ggtggctagc     360
ttgtttgcct ccctgctgcg gttttttcacc gaagttcatg ccagtccagc gttttttgcag    420
cagaaaagcc gccgacttcg gtttgcggtc gcgagtgaag atccctttct tgttaccgcc     480
aacgcgcaat atgccttgcg aggtcgcaaa atcggcgaaa ttccatacct gttcaccgac     540
gacggcgctg acgcgatcaa agacgcggtg atacatatcc agccatgcac actgatactc     600
ttcactccac atgtcggtgt acattgagtg cagcccggct aacgtatcca cgccgtattc     660
ggtgatgata atcggctgat gcagtttctc ctgccaggcc agaagttctt tttccagtac     720
cttctctgcc gtttccaaat cgccgctttg gacataccat ccgtaataac ggttcaggca     780
cagcacatca aagagatcgc tgatggtatc ggtgtgagcg tcgcagaaca ttacattgac     840
gcaggtgatc ggacgcgtcg ggtcgagttt acgcgttgct ccgccagtg gcgcgaaata     900
ttcccgtgca ccttgcggac gggtatccgg ttcgttggca atactccaca tcaccacgct     960
tgggtggttt ttgtcacgcg ctatcagctc tttaatcgcc tgtaagtgcg cttgctgagt    1020
ttccccgttg actgcctctt cgctgtacag ttctttcggc ttgttgcccg cttcgaaacc    1080
aatgcctaaa gacagctgaa agccgacagc agcagtttca tcaatcacca cgatgccatg    1140
ttcatctgcc cagtcgagca tctcttcagc gtaagggtaa tgcgaggtac ggtaggagtt    1200
ggccccaatc cagtccatta atgcgtggtc gtgcaccatc agcacgttat cgaatccttt    1260
gccacgtaag tccgcatctt catgacgacc aaagccagta agtagaacg tttgtggtt     1320
aatcaggaac tgttggccct tcactgccac tgaccggatg ccgacgcgaa gcgggtagat    1380
atcagactct gtctggcttt tggctgtgac ttcgagttca tagagataac cttcacccgg    1440
ttgccagagg tgcggattca ccacttgcaa agtcccgcta gtgccttgtc cagttgcaac    1500
cacctgttga tccgcatcac gcagttcaac gctgacatca ccattggcca ccacctgcca    1560
gtcaacagac gcgtggttac agtcttgcgc gacatgcgtc accacggtga tatcgtccac    1620
ccaggtgttc ggcgtggtgt agagcattac gctgcgatgg attccggcat agttaaagaa    1680
atcatgaag taagactgct tttcttgcc gttttcgtcg gtaatcacca ttcccggcgg    1740
gatagtctgc cagttcagtt cgttgttcac acaaacggtg atacgtacac ttttcccggc    1800
```

```
aataacatac ggcgtgacat cggcttcaaa tggcgtatag ccgccctgat gctccatcac   1860
ttcctgatta ttgacccaca ctttgccgta atgagtgacc gcatcgaaac gcagcacgat   1920
acgctggcct gcccaacctt tcggtataaa gacttcgcgc tgataccaga cgttgcccgc   1980
ataattacga atatctgcat cggcgaactg atcgttaaaa ctgcctggca cagcaattgc   2040
ccggctttct tgtaacgcgc tttcccacca acgctgatca attccacagt tttgcgatc    2100 cagactgaat gcccacaggc cgtcgagttt tttgatttca cggttggggg tttctacagg   2160
acggacgagt cgtcggttct gtaactatca tcatcatcat agacacacga aataaagtaa   2220
tcagattatc agttaaagct atgtaatatt tacaccataa ccaatcaatt aaaaaataga   2280
tcagtttaaa gaaagatcaa agctcaaaaa aataaaaaga gaaaagggtc ctaaccaaga   2340
aaatgaagga gaaaaactag aaatttaccc tcagatctac catggtcaag agtccccgt    2400 gttctctcca aatgaaatga acttccttat atagaggaag ggtcttgcga aggatagtgg   2460
gattgtgcgt catcccttac gtcagtggag atatcacatc aatccacttg ctttgaagac   2520
gtggttggaa cgtcttcttt ttccacgatg ctcctcgtgg gtggggtcc atctttggga    2580 ccactgtcgg cagaggcatc ttcaacgatg gcctttcctt tatcgcaatg atggcatttg   2640
taggagccac cttccttttc cactatcttc acaataaagt gacagatagc tgggcaatgg   2700
aatccgagga ggtttccgga tattaccctt tgttgaaaag tctcaattgc cctttggtct   2760
tctgagactg tatctttgat attttggag tagacaagtg tgtcgtgctc caccatgttg    2820
acgaagattt tcttcttgtc attgagtcgt aagagactct gtatgaactg ttcgccagtc   2880
tttacggcga gttctgttag gtcctctatt tgaatctttg actccatgaa gctaaactga   2940
aggcgggaaa cgacaatctg atccaagctc aagctgctct agcattcgcc attcaggctg   3000
cgcaactgtt gggaagggcg atcggtgcgg gcctcttcgc tattacgcca gctggcgaaa   3060
gggggatgtg ctgcaaggcg attaagttgg gtaacgccag ggttttccca gtcacgacgt   3120
tgtaaaacga cggccagtgc caagctatct ccatttaaat caacctaatt cgtaatcatg   3180
gtcatagctg tttcctgtgt gaaattgtta tccgctcaca attccacaca acatacgagc   3240
cggaagcata aagtgtaaag cctggggtgc ctaatgagtg agctaactca cattaattgc   3300
gttgcgctca ctgcccgctt tccagtcggg aaacctgtcg tgccagctgc attaatgaat   3360
cggccaacgc gcgggagag gcggtttgcg tattggctag agcagcttgc caacatggtg    3420
gagcacgaca ctctcgtcta ctccaagaat atcaaagata cagtctcaga agaccaaagg   3480
gctattgaga cttttcaaca aagggtaata tcgggaaacc tcctcggatt ccattgccca   3540
gctatctgtc acttcatcaa aaggacagta gaaaggaag gtggcaccta caaatgccat    3600
cattgcgata aaggaaaggc tatcgttcaa gatgcctctg ccgacagtgg tcccaaagat   3660
ggacccccac ccacgaggag catcgtggaa aagaagacg ttccaaccac gtcttcaaag    3720
caagtggatt gatgtgataa catggtggag cacgacactc tcgtctactc caagaatatc   3780
aaagatacag tctcagaaga ccaaagggct attgagactt ttcaacaaag ggtaatatcg   3840
ggaaacctcc tcggattcca ttgcccagct atctgtcact tcatcaaaag gacagtagaa   3900
aaggaaggtg gcacctacaa atgccatcat tgcgataaag gaaaggctat cgttcaagat   3960
gcctctgccg acagtggtcc caaagatgga cccccaccca cgaggagcat cgtggaaaaa   4020
gaagacgttc caaccacgtc ttcaaagcaa gtggattgat gtgatatctc cactgacgta   4080
agggatgacg cacaatccca ctatccttcg caagaccttc ctctatataa ggaagttcat   4140
```

```
ttcatttgga gaggacacgc tgaaatcacc agtctctctc tacaaatcta tctctctcga    4200
gctttcgcag atctgtcgat cgaccatgag caagacgaca gtaaggattg cgcaggtttc    4260
ggacgctcaa gccatccagg caatctacgc accaatggtt gagagcacta cgatttcgtt    4320
cgagcttgag ccgccttcag tcgaagagat ggccatgcgg attgagtcga ctctgctaac    4380
ttacccgtac ctggttgcgg tgcgagacgg ccaggtcatc ggctatgcat atgccagtca    4440
gcaccgggct cgtgaggcct atcgctggtc ggtcgacgtc accgtttata tatcgccaga    4500
agcgcaccgt agtggcgtcg gtcgggcact gtatgacgtg ttgctgccaa cattgaagaa    4560
gcaaggtttt cacgcagcct atgccgggat cgctctgccc aatgatggca gcgtgggact    4620
acacgaagca cttggcttcg ctcacattgg tacgtatcca gaagtaggat tcaagcatgg    4680
cgcttggcgt gatgttggat attggcgtat cgcgctggat tcaacgaatc cgccaaaact    4740
gcccgtgctt ttcagtgaga tcagtctctt ctgagcggga ctctggggtt cggatcgatc    4800
ctctagctag agtcgatcga caagctcgag tttctccata ataatgtgtg agtagttccc    4860
agataaggga attagggttc ctataggggtt tcgctcatgt gttgagcata taagaaaccc    4920
ttagtatgta tttgtatttg taaaatactt ctatcaataa aatttctaat tcctaaaacc    4980
aaaatccagt actaaaatcc agatcccccg aattaattcg gcgttaattc agtacattaa    5040
aaacgtcccg ggcaatgtgt tattaagttg tctaagcgtc aatttgttta caccagcata    5100
tatcctgcca                                                          5110
```